(12) United States Patent
Won

(10) Patent No.: US 7,504,477 B2
(45) Date of Patent: *Mar. 17, 2009

(54) POLYALKYLENE GLYCOL ACID ADDITIVES

(75) Inventor: Chee-Youb Won, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/386,876

(22) Filed: Mar. 22, 2006

(65) Prior Publication Data

US 2006/0167218 A1 Jul. 27, 2006

Related U.S. Application Data

(62) Division of application No. 10/625,033, filed on Jul. 22, 2003, now Pat. No. 7,193,031.

(60) Provisional application No. 60/398,137, filed on Jul. 24, 2002.

(51) Int. Cl.
*C08G 65/34* (2006.01)
*C08G 65/00* (2006.01)

(52) U.S. Cl. .................. 528/425; 528/271; 528/361; 514/1; 514/25; 424/193.1; 424/194.1

(58) Field of Classification Search ............... 528/425, 528/271, 361; 514/1, 25; 424/193.1, 194.1
See application file for complete search history.

(56) References Cited

U.S. PATENT DOCUMENTS

| 4,129,337 | A | 12/1978 | Hosaka et al. |
| 4,670,417 | A | 6/1987 | Iwasaki et al. |
| 5,672,662 | A | 9/1997 | Harris et al. |
| 6,495,659 | B2 | 12/2002 | Bentley et al. |
| 6,737,505 | B2 * | 5/2004 | Bentley et al. ............ 528/425 |
| 7,193,031 | B2 * | 3/2007 | Bailon et al. ............. 528/425 |

FOREIGN PATENT DOCUMENTS

| EP | 1064 951 | 1/2001 |
| JP | 63-208523 | 8/1988 |
| JP | 05-117300 | 5/1993 |
| JP | 06-192300 | 7/1994 |
| JP | 10-067800 | 3/1998 |
| JP | 2000-256211 | 9/2000 |
| JP | 2002-540065 | 11/2002 |
| JP | 2004-533598 | 11/2004 |
| WO | WO 97/03106 | 1/1997 |
| WO | WO 01/26692 | 4/2001 |
| WO | WO 01/46291 | 6/2001 |

OTHER PUBLICATIONS

Brenner, et. al.,(1978) Am. J. Physiol., 234, F455.
Zalipsky, et. al., and Harris et. al in Poly(ethylene glycol) Chemistry: Biotechnical and Biomedical Applications; J.M. Harris ed., Plenum Press: NY (1992), Chap. 21 and 22.
Monfardini, C., et. al., Bioconjugate Chemistry, Am Chem Soc, Wash, US, XP000494804, vol. 6, p. 62-69 (1995).

* cited by examiner

*Primary Examiner*—Duc Truong
(74) *Attorney, Agent, or Firm*—George W. Johnston; Dennis P. Tramaloni; Samuel H. Megerditchian

(57) ABSTRACT

A new class of activated polyalkylene glycol acids and their active ester reagents for conjugation to biopharmaceuticals such as polypeptides, sugars, proteins and therapeutically active small molecules to produce biologically active conjugates of these pharmaceuticals and methods for producing these conjugates.

16 Claims, No Drawings

POLYALKYLENE GLYCOL ACID ADDITIVES

This application is a division of U.S. application Ser. No. 10/625,033, filed Jul. 22, 2003, now U.S. Pat. No. 7,193,031; which claims the benefit of U.S. Provisional Application 60/398,137, filed Jul. 24, 2002. The entire contents of the above-identified applications are hereby incorporated by reference.

FIELD OF THE INVENTION

The field of the invention relates to polyalkylene glycol acids and their attachment to therapeutically active biopharmaceuticals for preparing therapeutically active polyalkylene glycol conjugates with these biopharmaceuticals.

BACKGROUND OF THE INVENTION

Chemical attachment of hydrophilic polyalkylene glycol linear polymers (known as PAG) to biopharmaceuticals such as proteins and peptides is well known and commonly used in biotechnology. The most common polyalkylene glycol molecule is polyethylene glycol polymer (known as PEG).

As an example of biotechnical application of PAG, some active derivatives of PAG have been attached to biopharmaceuticals such as proteins and enzymes with beneficial results. Since PAG is soluble in organic solvents, PAG attached to such biopharmaceuticals as enzymes or proteins can produce resulting conjugates that are soluble and active in organic solvents. Attachment of PAG to protein can reduce the immunogenicity and rate of kidney clearance of the PAG-protein conjugate as compared to the unmodified protein. In addition attachment of PAG to biopharmaceuticals such as protein can also dramatically increase the blood circulation lifetimes for these PAG conjugates.

In preparing PAG conjugates with biopharmaceuticals such as proteins the pharmacokinetics of the particular biopharmaceuticals will govern both the efficacy and duration of effect of the drug. In view of the immunogenicity, water insolubility and short in vivo half-life of biopharmaceuticals particularly proteins and polypeptides, it has become of major importance to reduce the rate of clearance of these biopharmaceuticals so that prolonged action can be achieved. This may be accomplished by retarding or inhibiting glomerular filtration which can be effected both by the charge on the protein and its molecular size (Brenner et al., (1978) Am. J. Physiol., 234, F455). By increasing the molecular volume and by masking potential epitope sites, modification of a therapeutic biopharmaceutical such as a polypeptide and a protein with a polymer has been shown to be efficacious in reducing both the rate of clearance as well as the antigenicity of the biopharmaceutical, especially proteins. Reduced proteolysis, increased water solubility, reduced renal clearance, and steric hindrance to receptor-mediated clearance are a number of mechanisms by which the attachment of a PAG polymer to the backbone of biopharmaceuticals such as polypeptides and proteins are beneficial in enhancing the pharmacokinetic properties of the drug Thus Davis et al., U.S. Pat. No. 4,129,337 discloses conjugating PEG to proteins such as enzymes and insulin to produce a less immunogenic product while retaining a substantial proportion of the biological activity of these biopharmaceuticals.

There are a large variety of active PAGs, particularly PEG, reagents which have been developed for the modification of biopharmaceuticals such as proteins (see for example Zalipsky, et al., and Harris et al. in: Poly(ethylene glycol) Chemistry: Biotechnical and Biomedical Applications; (J. M. Harris ed.) Plenum Press: New York, 1992; Chap. 21 and 22), most of which require the formation of a linking group between PEG and the biopharmaceuticals. Some of these reagents are unstable, to various degrees, in the aqueous medium in which the conjugation reaction occurs. In addition the conjugation process often results in the loss of in vitro biological activity which is due to several factors foremost of which being a steric interference with the proteins active site. A desired property therefore of a new reagent would be one that is not susceptible to degradation in an aqueous medium and one which may be employed to produce the site specific modification of a protein.

SUMMARY OF THE INVENTION

In accordance with this invention we have discovered a new class of activated polyalkylene glycol acids and their active ester reagents for conjugation to biopharmaceuticals such as polypeptides, sugars, proteins and therapeutically active small molecules. These reagents are those compounds which have any one of the following formulae:

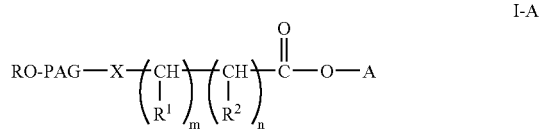

I-A wherein R, $R_1$ and $R_2$ are individually hydrogen or lower alkyl; X is —O— or —NH—; PAG is a divalent residue of polyalkylene glycol resulting from removal of both of its terminal hydroxy groups, which residue has a molecular weight of from 1,000 to 50,000 Daltons; n is an integer of from 0 to 1; m is an integer of from 4 to 8; and A is a hydrogen or an activated leaving group which when taken together with its attached oxygen atom forms an ester;

or hydrolyzable esters thereof wherein A is hydrogen.

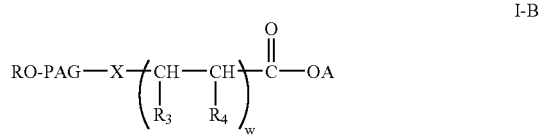

I-B wherein R, PAG, X and A are as above; w is an integer of from 1 to 3; and one of $R_3$ and $R_4$ is lower alkyl and the other is hydrogen or lower alkyl;

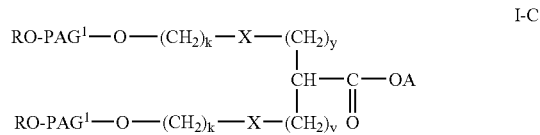

I-C wherein R, A, and X are as above, $PAG^1$ is a divalent residue of a polyalkylene glycol resulting from the removal of both of the terminal hydroxy groups, said residue having a molecular weight of from about 500 to about 25,000 Daltons, y is an integer from 0 to 3 and v is an integer from 1 to 3; and k is an integer from 1 to 2.

These compounds are useful reagents for forming conjugates with biopharmaceuticals such as polypeptides, sugars, proteins and glycosides. The compounds of formula I-A, I-B and I-C when they form conjugates with biopharmaceuticals such as proteins, peptides, and glycosides enhance their pharmacokinetic and pharmacodynamic properties. These clinically useful properties include longer in vivo circulating half-life, deceased clearance and enhanced potency, changes in bio-distribution leading to potential improvements in efficacy, reduced immunogenicity, reduced toxicity, better physical and thermal stability, protection against proteolytic degradation, among others. The stability of the compounds of formula I-A, I-B and I-C allow them to be easily conjugated to the biopharmaceutical.

DETAILED DESCRIPTION OF THE INVENTION

The reagents of formula I-A, I-B and I-C can be conjugated to the amino or hydroxy group of amino or hydroxy containing biopharmaceuticals to produce conjugates which retain a substantial portion of the biological activity of the biopharmaceutical from which they are derived. Generally for conjugation purposes, it is preferred that amino or hydroxy containing biopharmaceutical contain a terminal amino or hydroxy group. It is this terminal amino or hydroxy group through which the reagents of this invention can conjugate to produce the conjugates in accordance with this invention. The reagents of this invention are not susceptible to degradation in an aqueous medium and so they can be easily reacted with the biopharmaceutical to form the conjugate which can be administered for therapeutic purposes in an aqueous medium.

The term polyalkylene glycol designates poly(lower alkylene)glycol radicals where the alkylene radical is a straight or branched chain radical containing from 2 to 7 carbon atoms. The term "lower alkylene" designates a straight or branched chain divalent alkylene radical containing from 2 to 7 carbon atoms such as polyethylene, poly n-propylene, poly isopropylene, poly n-butylene, and polyisobutylene as well as polyalkylene glycols formed from mixed alkylene glycols such as polymers containing a mixture of polyethylene and polypropylene radicals and polymers containing a mixture of polyisopropylene, polyethylene and polyisobutylene radicals. The branched chain alkylene glycol radicals provide the lower alkyl groups in the polymer chain of from 2 to 4 carbon atoms depending on the number of carbon atoms contained in the straight chain of the alkylene group so that the total number of carbons atoms of any alkylene moiety which makes up the polyalkylene glycol substituent is from 2 to 7. The term "lower alkyl" includes lower alkyl groups containing from 1 to 7 carbon atoms, preferably from 1 to 4 carbon atoms, such as methyl, ethyl, propyl, isopropyl, etc. with methyl being especially preferred.

In accordance with the preferred embodiment of this invention, PAG in the compound in formulas I-A, I-B and I-C is polyethylene glycol residue formed by removal of the two terminal hydroxy groups. Further in accordance with this invention, the PAG residues in the compound of formula I-A and I-B, have molecular weights of from about 10,000 to about 50,000, most preferably from about 20,000 to about 40,000, with from about 25,000 to about 35,000 being especially preferred. In the compound of formula I-C, it is generally preferred that the two PAG1 radicals have a combined molecular weight of from about 10,000 to about 50,000 and preferably from about 20,000 to about 40,000, most preferably from about 25,000 to about 35,000.

The reagents of formula I-A, I-B and I-C can be conjugated to any conventional biopharmaceutical which contains a free hydroxy or amino group. Condensation can be either through the free acid or through the use of an activated ester.

In accordance with this invention, the compounds of formula I-A, I-B and I-C can be reacted with the free hydroxy group or free amino group of a biopharmaceutical which is a protein, peptide or small organic moiety to form either an ether or amide conjugate.

In accordance with this invention the ether or amide conjugates can be prepared from the compounds of the reagents of this invention by the following reaction schemes. In forming the ester conjugates, the reagents are reacted with a biopharmaceutical containing a terminal hydroxy group as illustrated below

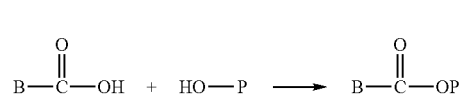

wherein P is a residue of a biopharmaceutical having a terminal hydroxy where the terminal hydroxy group is removed.

In this reaction scheme, B is a composite of compounds I-A, I-B and I-C without the terminal reactive acid or activated acid leaving group. In carrying out this reaction any conventional method of forming an ester by reacting a reactive acid group with an alcohol can be utilized to form the ester conjugate. Among the preferred methods is to couple the acid and alcohol in the presence of a coupling agent such as dicyclohexylcarbodiimide utilizing a coupling catalyst. Any conventional coupling catalyst such as 1-hydroxybenzotriazole and (4-dimethylamino)pyridine or mixtures thereof can be utilized. Generally this reaction is carried out in an inert organic solvent media. This reaction can be carried out with the free or activated ester derivative of this acid. If the activated acid derivative is utilized, then there is no need to utilize the coupling catalyst and/or the coupling agent. In carrying out this reaction temperature and pressure are not critical and this reaction can be carried out at room temperature. However, if desired, higher or lower temperatures can be utilized. In accordance with this reaction P can be the residue of any biopharmaceutical having a terminal hydroxy group. For forming the esters above among the preferred biopharmaceutical having a terminal hydroxy group are the nucleosides such as AZT. In addition P can be any such small molecule biopharmaceutical having a terminal hydroxy group.

In forming the amide, the compound of the following reaction is used

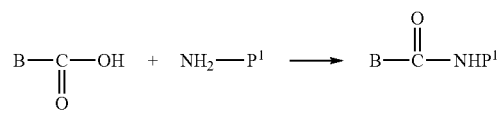

wherein $P^1$ is the residue of biopharmaceutical having a terminal amino group where this terminal amino group has been removed.

In the above reaction, scheme B is as described hereinbefore. In accordance with this reaction $P^1$ can be the residue of any biopharmaceutical having a terminal amino group such as protein or peptide or small molecule biopharmaceutical having a terminal amino group. Among the preferred protein and peptides are included interferon-α, interferon-β, consensus interferon, GCSF, GM-CSF, interleukins, colony stimulating factor as well as immunoglobulins such as IgG, IgE, IgM, IgA and IgD and fragments thereof. Other preferred amino biopharmaceuticals are those peptides set forth in U.S. Pat. No. 5,464,933 especially the T-20 peptide which has the structure: Tyr Thr Ser Leu Ile His Ser Leu Ile Glu Glu Ser Gln Asn Gln Gln Glu Lys Asn Glu Gln Glu Leu Leu Glu Leu Asp Lys Trp Ala Ser Leu Trp Asn Trp Phe (SEQ ID NO.: 1).

The reaction to produce the amide is carried out by utilizing any conventional means for coupling an acid or an activated acid derivative "OA" with an amide to form a peptide bond. Any conventional method of forming a peptide bond by the reaction of an acid and an amine to form an amide can be utilized in forming the conjugate.

In accordance with this invention, OA can be any conventional acid activating leaving group. Among the preferred acid activating leaving groups are the halogens such as chlorine and bromine, N-succinimidyloxy, sulfo-N-succinimidyloxy, 1-benzotriazolyloxy, 1-imidazolyl, p-nitrophenyloxy, 2,3,4-trichlorophenyloxy, pentachlorophenyloxy, pentafluorophenyloxy, N-phthalimidyloxy, N-tetrahydrophthalimide, N-glutarimide, 1-hydroxypiperidine, 5-chloro-8-hydroxyquinoline, N-norbornene-2,3-dicarboximide and hydroxy-7-azabenzotriazole.

A process is provided for producing an activated ester of the formula:

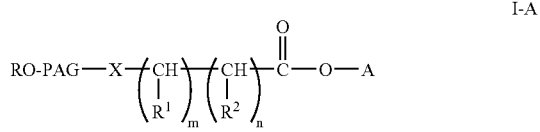

I-A wherein R, $R_1$ and $R_2$ are individually hydrogen or lower alkyl; X is —O— or —NH—; PAG is a divalent residue of polyalkylene glycol resulting from removal of both of its terminal hydroxy groups, which residue has a molecular weight of from 1,000 to 50,000 Daltons; n is an integer of from 0 to 1; m is an integer of from 4 to 8; and A is a hydrogen or an activated leaving group which when taken together with its attached oxygen atom forms an ester comprising, condensing a compound of the formula:

RO-PAG-V    V wherein R, and PAG are as above, and V is —OH or —$NH_2$, with the compound of the formula:

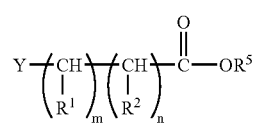

V1 wherein $R^5$ forms a hydrolyzable ester protecting group and Y is halide and $R^1$, $R^2$, m, and n, are as above, to produce an ester of the formula

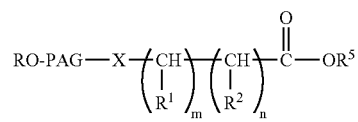

VIII wherein R, PAG, X, $R^1$, $R^2$, $R^5$, m and n are as above, hydrolyzing said ester to form a free acid of the formula:

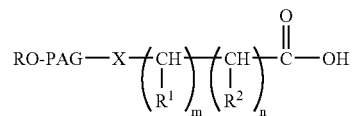

IX wherein R, PAG, X, $R^1$, $R^2$, m and n are as above, and reacting said free acid with a halide of an activated leaving group in the presence of a coupling agent to produce said activated ester.

The compound of formula I-A where X is 0 is

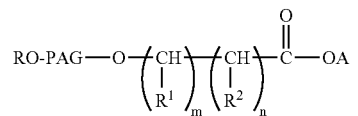

I-A1 wherein A, R, PAG, $R^1$, $R^2$, m and n are as above.

is prepared by reacting the PAG hydroxy compound of the formula

RO-PAG-OH    V wherein R, and PAG are as above
with a compound of the formula

V1 wherein $R^5$ forms a hydrolyzable ester protecting group and Y is halide and $R^1$, $R^2$, m, and n, are as above
via the following reaction scheme

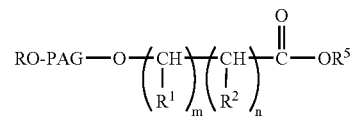

-continued

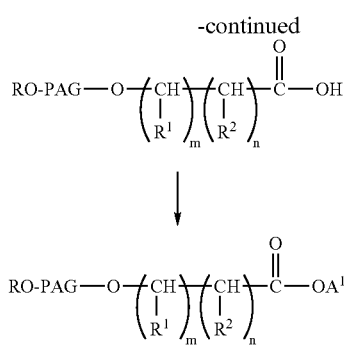

wherein R, PAG, m and n are as above and $A^1$ is an activated leaving group which when taken together with its attached oxygen forms an ester.

The compound of formula V when condensed with the compound of formula VI produces the compound of formula VIII. In this reaction the compound of formula V is reacted with the compound of formula VI by refluxing these compounds in an organic solvent in the presence of an alkali metal hydride such as sodium hydride. Any conventional method used in condensing an alcohol with a halide can be utilized in carrying out this reaction. Generally it is preferred to utilize as an inert organic solvent the aromatic hydrocarbon solvents such as benzene and toluene. However, any conventional inert organic solvent can be utilized to carry out this reaction. In the compound of formula VI, $R^3$ can be any conventional acid hydrolyzable ester protecting group. Generally, those hydrolyzable ester protecting groups include the lower alkyl ester protecting groups. The compound of formula VIII is hydrolyzed to the compound of formula IX by conventional means such as by basic hydrolysis with base such as an alkali metal hydroxide in a aqueous medium. The acid of formula IX is then converted to its activated form, the compound of formula X, through the use of an activating leaving group such as an N-hydroxy succinimidyl group by reaction with N-hydroxy succinimide. However, any conventional activating leaving groups such as those mentioned hereinbefore can be utilized in forming the compound of formula X. Any conventional method of converting a carboxylic acid into an activated ester containing an activating leaving group such as N-hydroxy succinimidyl group can be utilized to produce the compound of formula X.

In preparing the compound of formula I-A-1, which includes the compounds of formula IX and X, by condensing the formula V with the compound of formula VI by the aforementioned reaction scheme this reaction scheme can be further illustrated in the following general manner:

Five grams of PEG compound of formula V (molecular weight of 1000 to 40000) in 50 to 100 mL of toluene was azeotropically dried by refluxing for 1 to 3 hours, followed by the removal of 20 to 30 mL of toluene. The resulting mixture was dissolved in 20 to 30 mL of anhydrous tetrahydrofuran and added drop by drop to sodium hydride (5 to 10 fold molar excess) and anhydrous tetrahydrofuran (20~30 mL) in a round bottomed flask under argon flow. The resulting mixture was refluxed overnight. The following halo acid esters of Formula VI were used to prepare the compound of Formula VIII: Methyl 5-bromovalerate or (ethyl 5-iodovalerate; or, ethyl 6-bromohexanoate; ethyl-omega-chloro valerate; or 6-bromo hexanoic acid methyl ester; or methyl 7-bromoheptanoate; or ethyl 7-bromoheptanoate; or methyl 8-bromooctanoate; or ethyl 8-bromooctanoate; or methyl 10-bromodecanoate; or ethyl w-bromoundecanotate; or methyl 11-bromoundecanoate, or methyl bromomyristate; or ethyl 15-bromopentadecanoate; or 16-bromo-hecadecancarboxylic acid-methylester; or 17-bromo-hepadecancarboxylic acid-methylester; or methyl-3-chlorobutyrate, methyl 3-bromobutyrate; or ethyl 3-bromobutyrate, ethyl beta-bromovalerate; or ethyl beta-bromocaproate) (5 to 10 molar excess) was added to the reaction via syringe and the reaction was refluxed overnight. The reaction solution was then condensed by rotary evaporation. The residue containing the compound of formula VIII was precipitated by addition to the mixture of 2-propanol and diethyl ether (1:1). The precipitated product, the compound of formula VIII, was filtered off and dried in vacuo.

The PEG acid ester of formula VIII (4 g) was dissolved in 50 to 100 mL of 1N sodium hydroxide and the solution was stirred at room temperature overnight. The pH of the mixture was adjusted to 2.5 to 3.0 by addition of 1 to 6N hydrochloric acid, and the mixture was extracted with dichloromethane. The organic layer was dried over sodium sulfate, filtered, concentrated, and precipitated into diethyl ether. The PEG acid of formula IX was collected by filtration and dried under vacuum.

The PEG acid of formula IX (2 g) was dissolved in anhydrous dichloromethane (10 to 20 mL) followed by the addition of N-hydroxysuccinimide (1.05 to 2.0 fold molar excess) and dicyclohexylcarbodiimide (1.05 to 2.0 fold molar excess). The mixture was stirred overnight at room temperature under argon. The reaction mixture was filtered, concentrated, and precipitated with mixture of 2-propanol and diethyl ether (1:1). The product was dried in vacuo overnight to produce the activated ester of formula Ia1, the compound of formula X.

The compound of formula I-A where X is NH has the formula

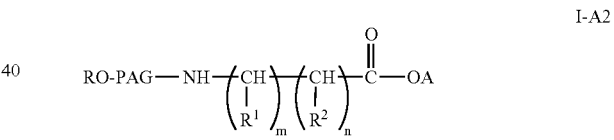

I-A2 wherein A, R, PAG, $R^1$, $R^2$, m and n are as above.

is prepared from the compound of

 XII wherein R and PAG are as above by first reacting the compound of formula XII with the compound of formula VI to produce a compound of the formula:

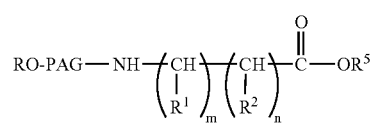

wherein R, $R^1$, $R^2$, $R^5$, PAG, m and n are as above.

The reaction to produce the compound of formula XIII is carried out by condensing the amine of formula XII with the halide of the compound of formula VI. Any conventional method of condensing an amine with a halide can be used in carrying out this reaction. The compound of formula XIII is converted to the compound of formula I-A2 when A is a leaving group via the intermediate

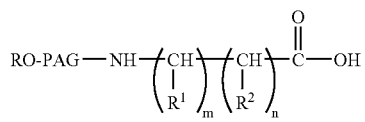

wherein R, PAG, $R^1$, $R^2$, m and n are as above.

This conversion to form the compound of formula XIV is carried by conventional basic hydrolysis as described hereinbefore. The compound of formula XIV is converted to the compound of formula 1A2 where A is an activated leaving group which when taken together with its attached oxygen forms an ester in the same manner as described in connection with the conversion of the compound of formula IX to the compound of formula X.

In general the method of producing the compound of formula 1-A2 where A is an activated leaving group which when taken together with its attached oxygen forms an ester by first reacting the compound of formula XII with the compound of formula VI to produce the compound of formula 1-A2 can be further illustrated by the following general reaction sequence:

Step One

Five grams of PEG amine of formula XII (molecular weight of 1000 to 40000) was dissolved in 25 to 50 mL of absolute ethanol. Then, the compound of formula VI which can be methyl 5-bromovalerate or (ethyl 5-iodovalerate, ethyl 6-bromohexanoate, or ethyl-omega-chloro valerate, or 6-bromo hexanoic acid methyl ester, or methyl 7-bromoheptanoate, or ethyl 7-bromoheptanoate, or methyl 8-bromooctanoate, or ethyl 8-bromooctanoate, or methyl 10-bromodecanoate, or ethyl w-bromoundecanotate, or methyl 11-bromoundecanoate, or methyl bromomyristate, or ethyl 15-bromopentadecanoate, or 16-bromo-hecadecancarboxylic acid-methylester, or 17-bromo-hepadecancarboxylic acid-methylester, or methyl-3-chlorobutyrate, or methyl 3-bromobutyrate, or ethyl 3-bromobutyrate, or ethyl beta-bromovalerate, or ethyl beta-bromocaproate) (5 to 10 molar excess) was added to the PEG solution. The resulting mixture was stirred at room temperature overnight. The reaction solution was then condensed by rotary evaporation. The residue was precipitated by addition to the mixture of 2-propanol and diethyl ether (1:1). The precipitated product was filtered off and dried in vacuo to produce the compound of formula XIII.

Step Two

PEG acid ester of formula XIII (4 g) was dissolved in 50 to 100 mL of 1N sodium hydroxide and the solution was stirred at room temperature overnight. The pH of the mixture was adjusted to 2.5 to 3.0 by addition of 1 to 6N hydrochloric acid, and the mixture was extracted with dichloromethane. The organic layer was dried over sodium sulfate, filtered, concentrated, and precipitated into diethyl ether. The product PEG acid of formula XIV, was collected by filtration and dried under vacuum.

The PEG acid of formula XIV (2 g) was dissolved in anhydrous dichloromethane (10 to 20 mL) followed by the addition of N-hydroxysuccinimide (1.05 to 2.0 fold molar excess) and dicyclohexylcarbodiimide (1.05 to 2.0 fold molar excess). The mixture was stirred overnight at room temperature under argon. The reaction mixture was filtered, concentrated, and precipitated with mixture of 2-propanol and diethyl ether (1:1). The product was dried in vacuo overnight to produce the compound of formula I-A2 where A is an activated leaving group which when taken together with its attached oxygen forms an ester.

A process is provided for producing an activated ester of the formula:

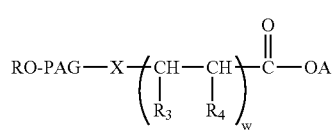

wherein R is hydrogen or lower alkyl; X is —O— or —NH—; PAG is a divalent residue of polyalkyleneglycol resulting from removal of both of its terminal hydroxy groups, which residue has a molecular weight of from 1,000 to 50,000 Daltons; w is an integer of from 1 to 3; and one of $R_3$ and $R_4$ is lower alkyl and the other is hydrogen or lower alkyl; and A is a hydrogen or an activated leaving group which when taken together with its attached oxygen atom forms an ester comprising, condensing a compound of the formula:

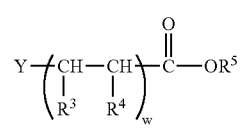

wherein w, Y, $R^3$, $R^4$ and $R^5$ are as above, Y is halide and $R^5$ forms a hydrolyzable protecting group, with a compound of the formula:

RO-PAG-V      V wherein R, and PAG are as above, V is —OH or —$NH_2$, to produce an ester of the formula:

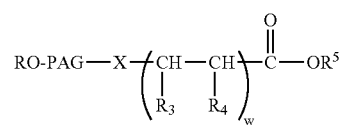

wherein w, R, PAG, X, $R^3$, $R^4$ and $R^5$ are as above hydrolyzing said ester to form a free acid of the formula:

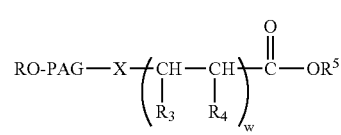

wherein R, PAG, X, $R^3$, $R^4$ and $R^5$ are as above, and reacting said free acid with a halide of an activated leaving group in the presence of a coupling agent to produce said activated ester.

The compound of formula I-B where X is 0 which has the formula

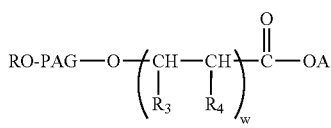
I-B1 wherein A, R, PAG, $R^3$, $R^4$, and w are as above is prepared by reacting the compound of formula V with the compound of formula

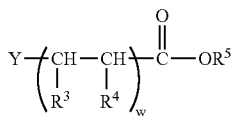
XX wherein w, $R^3$, $R^4$ and $R^5$ are as above, and Y is halide to produce a compound of the formula:

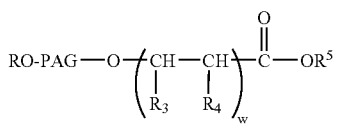
XXI wherein w, R, PAG, $R_3$, $R_4$ and $R_5$ are as above,

The reaction of the compound of formula XX with the compound of formula of formula V to produce the compound of formula XXI is carried out in the same manner as described in connection with the reaction of the compound of formula V and VI to produce the compound of formula VII. The compound of formula XXI is next subjected to basic hydrolysis utilizing the conditions described hereinbefore to form the compound of formula

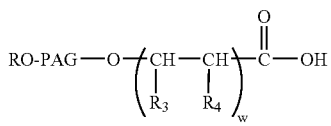
XXII wherein R, PAG, $R^3$ and $R^4$ are as above

The compound of formula XXII is next converted to the compound of formula I-B1 where A is an activated leaving group which when taken together with its attached oxygen forms an ester. This conversion is carried out in the same manner as described in connection with the formation of the compound of formula X from the compound of formula IX.

The compound of formula I-B where X is NH which has the formula

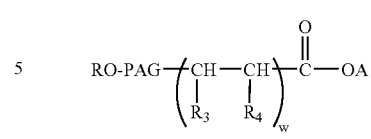
I-B2 wherein A, R, PAG, $R^3$ and $R^4$, and w are as above, is prepared by reacting the compound of formula XII with the compound of formula XX. This reaction produces a compound of the formula:

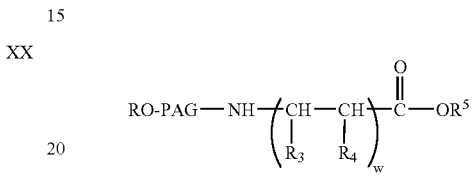
XXV wherein R, PAG, $R^3$, $R^4$ and $R^5$ are as above

The reaction of the compound of formula XX with the compound of formula XII to produce the compound of formula XXV is carried out in the same manner as described in connection with the reaction of the compound of formula XII with the compound of formula VI to produce the compound of formula XIII. The compound of formula XXV is next subjected to basic hydrolysis utilizing the conditions described hereinbefore to form the compound of formula

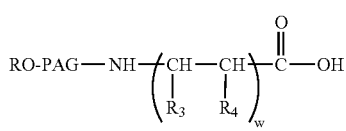
XXVI wherein R, PAG, $R^3$, $R^4$ and w are as above.

The formation of the compound of formula I-B2 by reaction of the compound of formula XX and the compound of formula III is carried out in the same manner as described in connection with the compound of formula I-A2 except that the compound of formula XX is substituted for the compound of formula VI.

A process is provided for producing an activated ester of the formula:

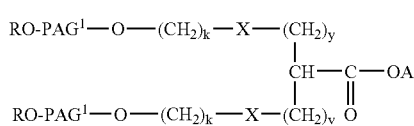
I-C1 wherein R is hydrogen or lower alkyl, X is —O— or —NH, A is a hydrogen or an activated leaving group which when taken together with its attached oxygen atom forms an ester, $PAG^1$ is a divalent residue of a polyalkylene glycol resulting from the removal of both of the terminal hydroxy groups, said residue having a molecular weight of from about 500 to about 25,000 Daltons, y is an integer from 0 to 3 and v is an integer from 1 to 3; and k is an integer from 1 to 2, comprising, condensing a compound of the formula:

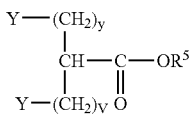

XXXV wherein Y is halide, y and v are as above, and $R^5$ forms a hydrolyzable ester protecting group with a compound of the formula

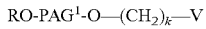 XXXVI wherein R, $PAG^1$ and k are as above, V is —OH or —$NH_2$, to produce an ester of the formula:

XXVII wherein R, $PAG^1$, X, $R^5$, k, v and y are as above, hydrolyzing said ester to form a free acid of the formula:

wherein R, $PAG^1$, X, k, v and y are as above, and reacting said free acid with a halide of an activated leaving group in the presence of a coupling agent to produce said activated ester.

The compound of formula I-C where X is 0 is the compound of the formula

I-C1 wherein R, $PAG^1$, A v, y and k are as above is prepared by the reaction of a compound of the formula

XXXV wherein Y, $R^5$, y and v are as above with a compound of the formula:

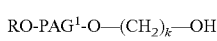 XXXVI wherein R, PAG and k are as above.

The formation of the compound of the formula I-C1 is carried out via the following reaction scheme:

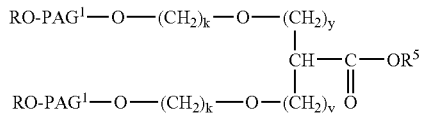

XXXVII

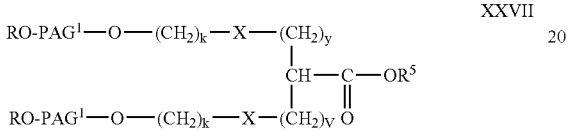

XXXVIII

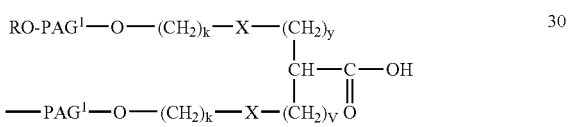

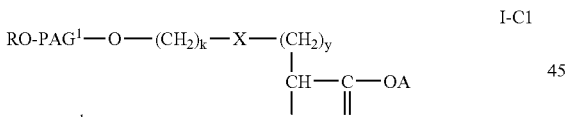

XXXIX wherein $A^1$, R, $PAG^1$, n and v are as above.

In the formation of the compound of formula I-C1 two moles of the compound of formula XXXVI are reacted with one mole of the compound of formula XXXV. This reaction is carried out using the same conditions as described in connection with the reaction of the compound of formula V and formula VI hereinbefore. In this manner, the compound of formula XXXVII is produced. The compound of formula XXXVII is hydrolyzed to form the compound of formula XXXVIII in the same manner as described in connection with the hydrolysis of formula VIII to the compound of formula IX. In the last step, the compound of formula XXXVIII is reacted to convert the carboxyl group to an activating leaving group in the same manner as described in connection with the formation of the compound of formula IX. In this manner the compound of formula XXXVIII is converted to the compound of formula 1-C1 where A is an activated leaving group which when taken together with its attached oxygen forms an ester.

The compound of formula I-C where X is NH, i.e., the compound of formula

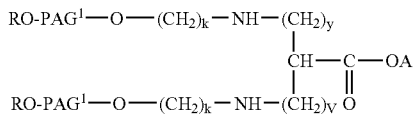

wherein A, R, PAG¹, v, w and y are as above is prepared by the reaction of a compound of the formula XXXV above with a compound of the formula

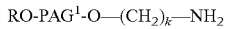

wherein R, PAG¹, and k are as above.

via the following reaction scheme

XXXV + XLI

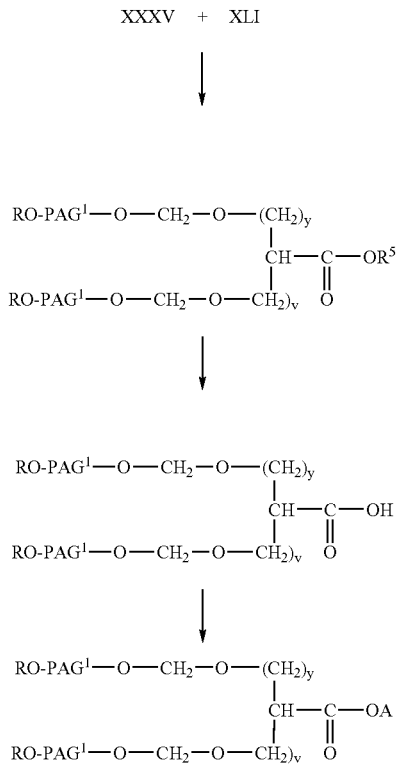

In the first step of this reaction, the compound of formula XXXV is reacted with the compound of formula XL1 to produce the compound of formula XLII. This reaction is carried out in the same manner as described in connection with the reaction of the compound of formula XII with the compound of formula VI to produce a compound of formula XIII. In the next step, the compound of XLII is hydrolyzed to the compound of formula XLIII in the same manner as described in connection with the hydrolysis of the compound of formula XIII. The compound of formula XLII is then reacted to convert the carboxyl group to an activating leaving group as described hereinbefore to produce the compound of formula I-C-2 where A is an activated leaving group which when taken together with its attached oxygen forms an ester. This reaction is carried out in the same manner as described in connection with the conversion of the compound of formula XIV to the compound of formula I-A2.

EXAMPLES

Example 1

Preparation of alpha-methoxy, omega-valeric acid succinimidyl ester of PEG

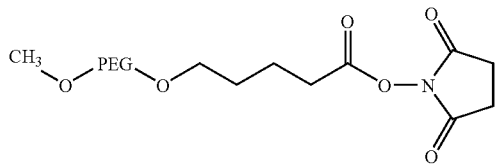

The compound of formula V where the R is methyl, PAG is PEG having a molecular weight of 10000 (5.0 g, 0.5 mmol) in 50 mL of toluene was azeotropically dried by refluxing for 2 hours, followed by the removal of 40 mL of toluene. The resulting mixture was dissolved in 30 mL of anhydrous tetrahydrofuran and added drop by drop to sodium hydride (0.12 g, 5 mmol) and anhydrous tetrahydrofuran (20 mL) in a round bottomed flask under argon flow. The resulting mixture was refluxed overnight. Ethyl-5-bromovalerate (0.79 mL, 5 mmol) was added to the reaction via syringe and the reaction was refluxed overnight. The reaction solution was then condensed by rotary evaporation. The residue was precipitated by addition to the mixture of 2-propanol and diethyl ether (1:1). The precipitated product was filtered off and dried in vacuo. Yield: 4.5 g. of the title compound where the PEG had a molecular weight of 1,000 [m-Peg Valeric ethyl ester].

m-PEG valeric acid ethyl ester (4 g) was dissolved in 100 mL of 1N sodium hydroxide and the solution was stirred at room temperature overnight. The pH of the mixture was adjusted to 2.5 by addition of 6N hydrochloric acid, and the mixture was extracted with dichloromethane (50 mL, 40 mL, and 30 mL). The organic layer was dried over sodium sulfate, filtered, concentrated, and precipitated into diethyl ether. The product m-PEG valeric acid where the PEG had a molecular weight of 1,000, was collected by filtration and dried under vacuum. Yield: 3 g. NMR (d6-DMSO): 1.50 ppm (q, 2H, —CH2CH2-COOH); 2.21 ppm (t, 2H, —CH2CH2-COOH); 3.21 ppm (s, —OCH3); 3.5 ppm (s, —O—CH2CH2-O—).

m-PEG valeric acid (2 g, 0.2 mmol) was dissolved in anhydrous dichloromethane (10 mL) followed by the addition of N-hydroxysuccinimide (47 mg, 0.41 mmol) and dicyclohexylcarbodiimide (87 mg, 0.42 mmol). The mixture was stirred overnight at room temperature under argon. The reaction mixture was filtered, concentrated, and precipitated with mixture of 2-propanol and diethyl ether (1:1). The product was dried in vacuo overnight. Yield: 1.6 g. of the title compound NMR (d6-DMSO): 1.58-1.67 ppm (m, 4H, —CH2CH2CH2COO—); 2.69 ppm (t, 2H, —CH2CH2CH2-

COO—); 2.81 ppm (s, 4H, NHS); 3.21 ppm (s, —OCH3); 3.5 ppm (s, —O—CH2CH2-O—).

Example 2

Preparation of alpha-methoxy, omega-beta Butanoic Acid Succinimidyl Ester of PEG

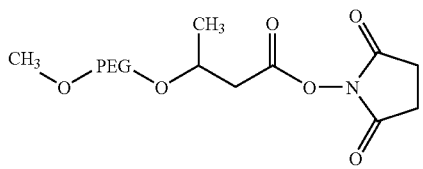

The methoxy compound of formula I where PAG was PIG having a molecular weight 10000 (5.0 g, 0.5 mmol) in 50 mL of toluene was azeotropically dried by refluxing for 2 hours, followed by the removal of 40 mL of toluene. The resulting mixture was dissolved in 30 mL of anhydrous tetrahydrofuran and added drop by drop to sodium hydride (0.12 g, 5 mmol) and anhydrous tetrahydrofuran (20 mL) in a round bottomed flask under argon flow. The resulting mixture was refluxed overnight. Ethyl-beta-bromobutyrate (0.74 mL, 5 mmol) was added to the reaction via syringe and the reaction was refluxed overnight. The reaction solution was then condensed by rotary evaporation. The residue was precipitated by addition to the mixture of 2-propanol and diethyl ether (1:1) to produce the methyl PEG where betahydrate ethyl ester PEG has a molecular weight of 1,000. The precipitated product was filtered off and dried in vacuo. Yield: 4.5 g. NMR (d6-DMSO): 0.83 ppm (t, 3H, —O—CH2-CH3); 1.05 ppm (t, 3H, —CH3); 1.57 ppm (m, 1H, —CHCH2CO—); 3.21 ppm (s, —OCH3); 3.5 ppm (s, —O—CH2CH2-O—).

m-PEG ethyl-beta butyrate (3 g) was dissolved in 50 mL of 1N sodium hydroxide and the solution was stirred at room temperature overnight. The pH of the mixture was adjusted to 2.5 by addition of 6N hydrochloric acid, and the mixture was extracted with dichloromethane (25 mL, 20 mL, and 20 mL). The organic layer was dried over sodium sulfate, filtered, concentrated, and precipitated into diethyl ether. The product m-PEG valeric acid was collected by filtration and dried under vacuum. Yield: 2.4 g. NMR (d6-DMSO): 0.88 ppm (t, 3H, —CH3), 1.61 ppm (m, 1H, —CHCH2CO—); 3.21 ppm (s, —OCH3); 3.5 ppm (s, —O—CH2CH2-O—) to produce the methoxy PEG butanoic acid where PEG had a molecular weight 41,000.

m-PEG10k-beta-butanoic acid (1 g, 0.1 mmol) was dissolved in anhydrous dichloromethane (5 mL) followed by the addition of N-hydroxysuccinimide (24 mg, 0.20 mmol) and dicyclohexylcarbodiimide (43 mg, 0.21 mmol). The mixture was stirred overnight at room temperature under argon. The reaction mixture was filtered, concentrated, and precipitated with mixture of 2-propanol and diethyl ether (1:1). The product was dried in vacuo overnight to yield 6.6 g of the title compound where the PEG had a molecular weight of 13000.

Example 3

Preparation of PEG-AZT Conjugate

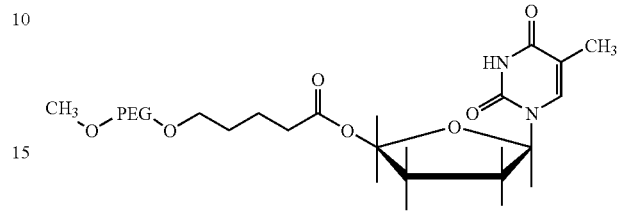

m-PEG10K valeric acid in Example 1 (0.2 g, 0.02 mmol) was dissolved in anhydrous dimethylformamide (2 mL) followed by the addition of 3'-Azido-3'-deoxy-thymidine (AZT) (10.7 mg, 0.04 mmol), 1-Hydroxybenzotriazole (HOBT) (9.8 mg, 0.04 mmol), (4-dimethylamino)pyridine (DMAP) (5.7 mg, 0.042 mmol), and dicyclohexylcarbodiimide (DCC) (9.5 mg, 0.046 mmol). The mixture was stirred overnight at room temperature under argon. The reaction mixture was filtered, concentrated, and precipitated with mixture of 2-propanol and diethyl ether (1:1). The product was dried in vacuo overnight. Yield: 0.17 g. NMR (d6-DMSO): 1.18 ppm (m, 3H, H1); 1.51 ppm (m, 2H, H9); 2.23 ppm (m, 1H, H4); 2.37 ppm (t, 2H, H8); 3.21 ppm (s, H12); 3.5 ppm (s, H11). 4.2 ppm (m, 1H, H5); 6.12 ppm (m, H3, H6); 7.45 ppm (s, 1H, H2); 11.35 ppm (br, 1H, H10).

Example 4

Pegylation of T-20 with mPEG10k-SVA

Alpha-methoxy, omega-valeric acid succinimidyl ester of PEG 10 kDa prepared according to Example 1 was added to 20 mg of T-20 which has the sequence:

Tyr Thr Ser Leu Ile His Ser Leu Ile Glu Glu Ser Gln Asn Gln Gln Glu Lys Asn Glu Gln Glu Leu Leu Glu Leu Asp Lys Trp Ala Ser Leu Trp Asn Trp Phe (SEQ ID NO:1)

This addition was carried out in 1.0 ml of buffer (50 mM borate pH 8.0) in a molar ratio of 2 moles of reagent per one mole of T-20. The solution was stirred for 4 hours at room temperature. Pegylated T-20 was purified from the reaction mixture using ion exchange chromatography (QA). A step gradient with increasing salt concentrations from 100 mM to 1 M NaCl in 20 mM Tris, pH 7.5 was used to separate pegylated T-20 and unmodified T-20.

Example 5

Pegylation of EPO with mPEG30K-β-SBA

1. Fermentation and Purification of Human EPO

Note: The methods for the fermentation and purification of human EPO were exactly the same as the one which was described in European Patent Application (EP 1 064 951 A2). (See Page 7-9)

2. Pegylation Reaction

To five milligrams of EPOsf (653 μL of a 7.66 mg/ml EPOsf stock, 0.274 μmol) 347 μL of 100 mM borate buffer, pH 8.0 containing 8.2 mg of 30 kDa methoxy-PEG-β-SBA (0.274 μmol) was added and mixed for 4 h at 4° C. The final protein concentration was 5 mg/ml and the protein:PEG reagent ratio was 1:1. After four hours, the reaction was stopped by adjusting the pH to 4.5 with glacial acetic acid and stored at −20° C., until ready for purification.

3. Purification

The reaction mixture from the previous step was diluted 1:5 with 10 mM sodium acetate, pH 4.5 and applied to 100 ml SP-Sepharose FF (sulfopropyl cation exchange resin) packed into a 18 mm×143 mm column. The column was previously equilibrated with the same buffer. Column effluents were monitored at 280 nm with a Gilson UV monitor and recorded with a Kipp and Zonen recorder. The column was washed with 100 ml or 1 bed volume of equilibration buffer to remove excess reagents, reaction byproducts and oligomeric PEG-EPO. It was followed by washing with 2 bed volumes of 100 mM NaCl to remove di-PEG-EPO. Mono-PEG-EPO was then eluted with 200 mM NaCl. During elution of the mono-PEG-EPO, the first 50 ml of the protein peak was discarded and the mono-PEG-EPO was collected as a 150 ml fraction. Unmodified EPOsf remaining on the column was eluted with 750 mM NaCl. All elution buffers were made in the equilibration buffer. The eluted sample was analyzed by SDS-PAGE and MALDI-TOF. The mono-PEG-EPO pool obtained from the 150 ml fraction, which had no detectable unmodified EPOsf, was then concentrated ~5.0 mg/ml and diafiltered into the storage buffer, 10 mM potassium phosphate, 100 mM NaCl, pH 7.5. Concentration/Diafiltration was performed with Millipore Labscale™ TFF System fitted with 5 kDa cut off Millipore Pellicon XL Biomax 50 membrane at ambient temperature. Concentrated mono-PEG-EPO was sterile filtered and stored frozen at −20° C.

Example 6

Pegylation of EPO with mPEG10K-SVA

A different aliquot of the EPOsf used in Example 5 was reacted with 10 kDa methoxy-PEG-SVA. Reaction was performed at a protein:reagent ratio of 1:2 and purification techniques were in accordance with Example 5.

Example 7

In-vivo activity of pegylated EPO determined by the normocythaemic mouse assay.

The normocythaemic mouse bioassay is known in the art (Pharm. Europa Spec. Issue Erythropoietin BRP Bio 1997 (2)) and a method in the monography of erythropoietin of Ph. Eur. BRP. The sample were diluted with BSA-PBS. Normal healthy mice, 7-15 weeks old, were administered s.c. 0.5 ml of the EPO-fraction containing unpegylated EPO (40 ng/mouse) or mono-pegylated EPO (10 or 40 ng/mouse) from Example 5 or 6. Over a period of 6 days, blood was drawn by puncture of the tail vein and diluted such that 1 μL of blood was present in 1 ml of an 0.15 mol acridine orange staining solution. The staining time was 3 to 10 minutes. The reticulocyte counts were given in terms of absolute figures (per 30,000 blood cells analyzed). For the data presented, each group consisted of 5 mice per day, and the mice were bled only once. The results show the superior activity and the prolonged half life of the pegylated EPO species indicated by the significantly increased amounts of reticulocytes and the shift of the reticulocytes count maximum using the same dose per mouse (10 ng), compared to a dose of 40 ng for unmodified EPO.

Example 8

Preparation of Methoxy Branched PEG-Acid and its Succinimidyl Ester

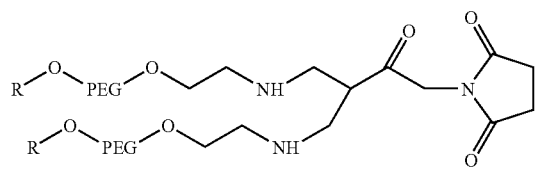

The compound of formula VI where the PAG is PEG having a molecular weight of 1,000 [m-Peg amine of molecular weight 10000] (1.0 g, 0.1 mmol) was dissolved in 5 mL of absolute ethanol at 40° C. followed by the addition of ethyl-3-bromo-2-(bromomethyl)propionate (7.6 TL, 0.048 mmol), and the mixture was stirred overnight at 40° C. under argon. The reaction solution was condensed by rotary evaporation. The residue was precipitated by addition to the mixture of 2-propanol and diethyl ether (1:1). The precipitated product was filtered off and dried in vacuo. Yield: 0.89 g.

Branched m-Peg acid ester (0.89 g) was dissolved in 20 mL of 1N sodium hydroxide and the solution was stirred at room temperature overnight. The pH of the mixture was adjusted to 2.5 by addition of 6N hydrochloric acid, and the mixture was extracted with dichloromethane (10 mL, 5 mL and 5 mL). The organic layer was dried over sodium sulfate, filtered, concentrated, and precipitated into diethyl ether. The product m-Peg valeric acid was collected by filtration and dried under vacuum. Yield: 0.64 g.

Branched m-Peg acid (0.64 g, 0.032 mmol) was dissolved in anhydrous dichloromethane (5 mL) followed by the addition of N-hydroxysuccinimide (11 mg, 0.098 mmol) and dicyclohexylcarbodiimide (20 mg, 0.099 mmol). The mixture was stirred overnight at room temperature under argon. The reaction mixture was filtered, concentrated and precipitated with mixture of 2-propanol and diethyl ether (1:1). The product was dried in vacuo overnight. Yield: 0.58 g.

Example 9

Preparation of Branched PEG-Acid and its Succinimidyl Ester

The methoxy PAG compound of formula V where the PAG is PEG having a molecular weight of 2,000 [m-Peg amine of molecular weight 10000] (1.0 g, 0.1 mmol) was dissolved in 5 mL of absolute ethanol at 40° C. followed by the addition of ethyl-3-bromo-2-(bromomethyl)propionate (7.6 TL, 0.048 mmol), and the mixture was stirred overnight at 40° C. under argon. The reaction solution was condensed by rotary evaporation. The residue was precipitated by addition to the mixture of 2-propanol and diethyl ether (1:1). The precipitated product was filtered off and dried in vacuo. Yield: 0.89 g.

Branched m-Peg acid ester (0.89 g) was dissolved in 20 mL of 1N sodium hydroxide and the solution was stirred at room temperature overnight. The pH of the mixture was adjusted to 2.5 by addition of 6N hydrochloric acid, and the mixture was extracted with dichloromethane (10 mL, 5 mL and 5 mL). The organic layer was dried over sodium sulfate, filtered, concentrated, and precipitated into diethyl ether. The product m-Peg valeric acid was collected by filtration and dried under vacuum. Yield: 0.64 g.

Branched m-Peg acid (0.64 g, 0.032 mmol) was dissolved in anhydrous dichloromethane (5 mL) followed by the addition of N-hydroxysuccinimide (11 mg, 0.098 mmol) and dicyclohexylcarbodiimide (20 mg, 0.099 mmol). The mixture was stirred overnight at room temperature under argon. The reaction mixture was filtered, concentrated and precipitated with mixture of 2-propanol and diethyl ether (1:1). The product was dried in vacuo overnight. Yield: 0.58 g of the title compound.

What is claimed is:

1. The compound of formula

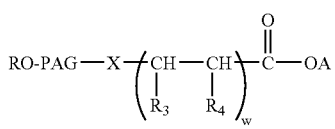

I-B wherein R is hydrogen or lower alkyl; X is —O— or —NH—; PAG is a divalent residue of polyalkylene glycol resulting from removal of both of its terminal hydroxy groups, which residue has a molecular weight of from 1,000 to 50,000 Daltons; w is an integer of from 1 to 3; and one of $R_3$ and $R_4$ is lower alkyl and the other is hydrogen or lower alkyl; and A is a hydrogen or an activated leaving group which when taken together with its attached oxygen forms an ester;

or hydrolyzable esters thereof wherein A is hydrogen.

2. The compound of claim 1 wherein said compound is

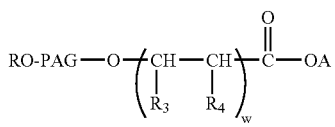

I-B1 wherein A, R, PAG, $R^3$, $R^4$, w and n are as above.

3. The compound of claim 2 wherein A is hydrogen.

4. The compound of claim 3 wherein PAG is PEG, a divalent polyethylene glycol residue resulting from the removal of both of its terminal hydroxy groups.

5. The compound of claim 4 wherein R is methyl.

6. The compound of claim 5 wherein w is 1.

7. The compound of claim 6 wherein PEG has a molecular weight of from 10,000 to 40,000.

8. The compound of claim 7 wherein PEG has a molecular weight of from 20,000 to about 35,000.

9. The compound of claim 2 wherein A is an activated leaving group.

10. The compound of claim 9 wherein PAG is PEG, a divalent polyethylene glycol residue resulting from the removal of both of its terminal hydroxy groups.

11. The compound of claim 10 wherein R is methyl.

12. The compound of claim 11 wherein w is 1.

13. The compound of claim 12 wherein PEG has a molecular weight of from 10,000 to 40,000.

14. The compound of claim 13 wherein PEG has a molecular weight of from 20,000 to about 35,000.

15. A process for producing an activated ester of the formula:

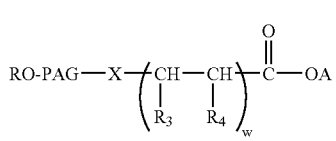

I-B wherein R is hydrogen or lower alkyl; X is —O— or —NH—; PAG is a divalent residue of polyalkyleneglycol resulting from removal of both of its terminal hydroxy groups, which residue has a molecular weight of from 1,000 to 50,000 Daltons; w is an integer of from 1 to 3; and one of $R_3$ and $R_4$ is lower alkyl and the other is hydrogen or lower alkyl; and A is a hydrogen or an activated leaving group which when taken together with its attached oxygen atom forms an ester comprising, condensing a compound of the formula:

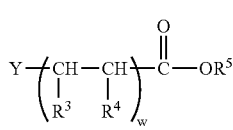

XX wherein w, Y, $R^3$, $R^4$ and $R^5$ are as above, Y is halide and $R^5$ forms a hydrolyzable protecting group
with a compound of the formula:

RO-PAG-V

V wherein R, and PAG are as above, V is —OH or —NH$_2$, to produce an ester of the formula:

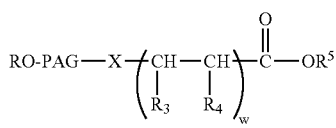

XXI wherein w, R, PAG, X, $R^3$, $R^4$ and $R^5$ are as above hydrolyzing said ester to form a free acid of the formula:

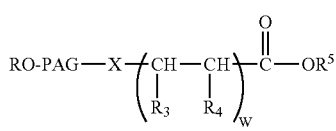

XXII wherein R, PAG, X, $R^3$, $R^4$ and $R^5$ are as above, and reacting said free acid with a halide of an activated leaving group in the presence of a coupling agent to produce said activated ester.

16. The process of claim 15 wherein said leaving group is a N-hydroxysuccinimidyl group.

* * * * *